United States Patent [19]

Tadanier et al.

[11] 4,205,070
[45] May 27, 1980

[54] 6'N-ALKYL- AND 6',6'-DI-N-ALKYL DERIVATIVES OF FORTIMICINS A AND B

[75] Inventors: John S. Tadanier, Waukegan; Daniel A. Dunnigan, Winthrop Harbor; Leslie A. Freiberg; Jerry R. Martin, both of Waukegan, all of Ill.

[73] Assignee: Abbott Laboratories, North Chicago, Ill.

[21] Appl. No.: 863,018

[22] Filed: Dec. 21, 1977

[51] Int. Cl.² .................. A61K 31/71; C07H 15/22
[52] U.S. Cl. .................. 424/180; 536/17 R; 536/4
[58] Field of Search .............. 536/17, 13; 424/180

[56] References Cited
U.S. PATENT DOCUMENTS

| | | | |
|---|---|---|---|
| 3,929,762 | 12/1975 | Umezawa et al. | 536/17 |
| 3,931,400 | 1/1976 | Nara et al. | 424/118 |
| 3,976,768 | 8/1976 | Nara et al. | 424/118 |

Primary Examiner—Johnnie R. Brown
Attorney, Agent, or Firm—Robert L. Niblack; Gildo E. Fato; Joyce R. Niblack

[57] ABSTRACT

Novel fortimicin antibiotics represented by the formula

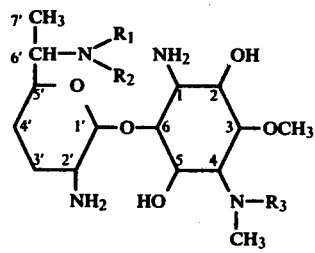

wherein $R_1$ is loweralkyl, $R_2$ is hydrogen or loweralkyl and $R_3$ is selected from the group consisting of hydrogen, acyl, hydroxyacyl, aminoacyl, N-monoloweralkylaminoacyl, N,N-diloweralkylaminoacyl, hydroxy-substituted aminoacyl or an aminoacid residue, loweralkyl, hydroxyloweralkyl, aminoloweralkyl, N-monoloweralkylaminoloweralkyl, N,N-diloweralkylaminoloweralkyl or hydroxy-substituted aminoloweralkyl; and the pharmaceutically acceptable salts thereof, intermediates useful in their preparation, compositions employing the compounds and methods of using the compounds.

29 Claims, No Drawings

6'N-ALKYL- AND 6',6'-DI-N-ALKYL DERIVATIVES OF FORTIMICINS A AND B

BACKGROUND OF THE INVENTION

Antibiotic therapy plays a vital role in modern medicine. The advent of antibiotic therapy in this century has, in part, been responsible for the increased life expectancy, as wel Despite the availability of a variety of highly effective antibiotics, the search for improved agents is a continuing one for a variety of reasons. Many organisms become resistant to a particular antibiotic or class of antibiotics and thus new drug entities must be continually made available to treat infections involving strains of organisms which have become resistant to all other therapy. Apart from the problem of resistance, this powerful class of drugs has a number of undesirable side effects and thus the search continues for agents which are lower in toxicity than presently available antibiotics yet are effective antimicrobial agents.

Another problem with current antibiotic therapy is that there are certain organisms, such as the Proteus genus which are very difficult to eradicate. Thus researchers are constantly seeking new antibiotic entities which would be effective against various Proteus strains as well as strains of other pathogenic organisms.

Recently a new group of antibiotics has been identified and designated as the fortimicins.

Fortimicin A exhibits a wide range of in vitro activity against gram-positive and gram-negative bacteria and also exhibits excellent activity against strains of *Staphylococcus aureus* and *Escherichia coli* which are resistant to various known antibiotics such as kanamycin, gentamicin, tobramycin and the like, as well as exhibiting antibacterial activity against bacteria of the genus Proteus. In vivo tests indicate the $ED_{50}$ of fortimicin A against *Escherichia coli* Juhl KY 4286 in mice to be 6 mg/kg (See U.S. Pat. No. 3,976,768).

Fortimicin B also exhibits in vitro antibacterial activity against various gram-positive and gram-negative antibiotics, but is considerably less active than fortimicin A. (See U.S. Pat. No. 3,931,400.) 4-N-Acyl and 4-N-alkyl derivatives of fortimicin B have also been developed.

Just as there has been a continuing need for new generations of aminoglycosides, penicillins, cephalosporins and other important antibiotics, there is a need for various fortimicin derivatives.

The present invention provides new derivatives of fortimicin A, fortimicin B, 4-N-acyl fortimicin B and 4-N-alkyl fortimicin B.

SUMMARY OF THE INVENTION

The present invention provides a novel series of 6'-N-alkyl and 6', 6'-di-N-alkyl derivatives of fortimicin A, fortimicin B, 4-N-acyl fortimicin B and 4-N-alkyl fortimicin B. The compounds are useful as broad-spectrum antibiotics, as anti-bacterial scrub solutions for sterilization, for example, laboratory benchtops, surfaces in operating rooms and the like and as intermediates in preparing other useful fortimicin derivatives.

DETAILED DESCRIPTION OF THE INVENTION

The compounds of this invention are represented by Formula I.

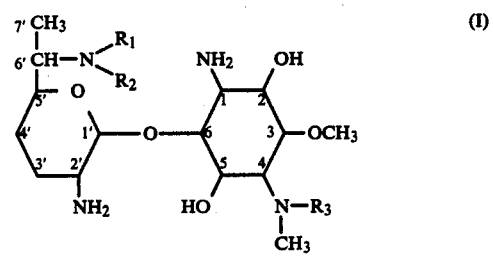

wherein $R_1$ is loweralkyl, $R_2$ is hydrogen or loweralkyl and $R_3$ is selected from the group consisting of hydrogen, acyl, hydroxyacyl, aminoacyl, N-monoloweralkylaminoacyl, N,N-diloweralkylaminoacyl, hydroxy-substituted aminoacyl, an amino acid residue, or a loweralkyl, hydroxyloweralkyl, aminoloweralkyl, N-monoloweralkylaminoalkyl, N, N-diloweralkylaminoloweralkyl or hydroxy-substituted-aminoloweralkyl and the pharmaceutically acceptable salts thereof.

The compounds are useful as antibiotics, antibacterial scrub solutions and as intermediates for synthesizing other useful fortimicin derivatives.

The term "loweralkyl" as used herein refers to straight or branched chain alkyl radicals having from 1 to 7 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl, n-heptyl and the like.

The term "acyl" as used herein, refers to groups represented by the formula

wherein R is loweralkyl, aminoloweralkyl, N-substituted aminoloweralkyl and N,N-disubstituted aminoloweralkyl wherein the N-substituents are loweralkyl groups such as methyl or ethyl.

In the case of $R_4$, the acyl group can be derived from naturally occurring amino acids such as histidine, phenylalanine, sarcosine, tyrosine, valine, alanine, leucine, isoleucine, aspartic acid, asparginine, threonine, methionine, glutamine, glutamic acid, and the like.

The term "small peptide" refers to di- or tripeptides such as glycyl-glycine, glutamyl-alanine or other di- or tri-peptides.

The term "pharmaceutically acceptable salts" as used herein, refers to the non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

Intermediates useful in the practice of this invention for preparing the compounds of Formula I are represented by Formulae II:

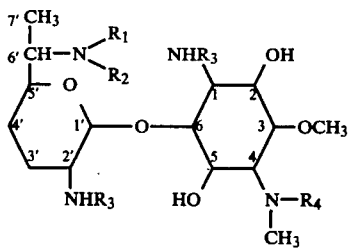 (II)

wherein $R_1$ is aryl or loweralkyl, $R_2$ is hydrogen or loweralkyl; each $R_3$ is aryloxycarbonyl and $R_4$ is hydrogen, aryloxycarbonylglycyl, aryloxycarbonylacyl or

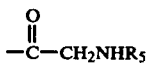

wherein $R_5$ is hydrogen or aryloxycarbonyl.

The term "aryloxycarbonylacyl" refers to acyl or substituted acyl groups referred to in the definition of $R_4$ in Formula I containing an amine group which requires protection during synthesis of the final products of Formula I, such as alanine, sarcosine and the like. The preferred aryloxycarbonyl protecting group is benzyloxycarbonyl, however, it will be apparent to those skilled in the art that other protecting groups such as chlorobenzyloxycarbonyl, bromobenzyloxycarbonyl and the like can be employed in the practice of this invention.

The letter "Z", when used herein, refers to benzyloxycarbonyl.

Generally speaking the compounds of this invention can be prepared by initially converting fortimicin B to 1,2-di-N-benzyloxycarbonylfortimicin B by, for example, treatment with a suitable acylating agent such as N-benzyloxycarbobenzyloxy succinimide. 1,2'-Di-N-benzyloxycarbonyl fortimicin B is then treated with an aromatic aldehyde such as benzaldehyde, followed by treatment with a suitable metal hydride reducing agent such as sodium borohydride, zinc borohydride, or lithium borohydride, resulting in a 6'-arylmethyl derivative. For example, when the aromatic aldehyde chosen is benzaldehyde, the resulting intermediate is 1,2'-di-N-benzyloxycarbonyl-6'-N-benzylfortimicin B. The 6'-N-benzyl derivative can then be subjected to reductive alkylation with an aliphatic aldehyde such as formaldehyde, acetaldehyde, propionaldehyde, butyraldehyde, etc., and the resulting product is subjected to hydrolysis in the presence of an aldehyde scavenger such as hydroxylamine hydrochloride or methoxylamine hydrochloride to obtain the desired 1,2'-di-N-benzyloxycarbonyl-6'-N-benzyl-6'-N-loweralkylfortimicin B in which the 6'-N-loweralkyl group is derived from the aliphatic aldehyde chosen. For example, reductive alkylation with formaldehyde results in the 6'-N-loweralkyl group being methyl, and the resulting product is 1,2'-di-N-benzyloxycarbonyl-6'-N-benzyl-6'-N-methylfortimicin B. With acetaldehyde the 6'-N-loweralkyl group is ethyl, and the product is 1,2'-di-N-benzyloxycarbonyl-6'-N-benzyl-6'-N-ethylfortimicin B, etc.

The C4-N-methylamino group of 1,2'-di-N-benzyloxycarbonyl-6'-N-benzyl-6'-N-alkylfortimicin B can be conveniently acylated with, for example, an activated carboxylic acid derivative such as a carboxylic acid anhydride, a carboxylic acid derivative such as a carboxylic acid ester or a carboxylic acid azide, following the methodology commonly used in peptide synthesis to obtain the corresponding 4-N-acyl intermediates. The above referred to active carboxylic acid esters can be prepared by reacting the appropriate carboxylic acid,

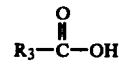

with, for example, 1-hydroxy benzotriazole-N-hydroxysuccinimide, N-hydroxy-5-norborene-2,3-dicarboximide according to the method of Fugino et al., *Chem. Pharm. Bull Japan,* 22, 1857 (1974). For example, when the acylating agent N-hydroxysuccinimide ester of N-benzyloxycarbonylglycine is reacted with 1,2'-di-N-benzyloxycarbonyl-6'-N-benzyl-6'-N-methylfortimicin B, the resulting product is tri-N-benzyloxycarbonyl-6'-N-benzyl-6'-N-methylfortimicin A. If, for example, the acylating agents are the N-hydroxysuccinimide esters of N-benzyloxycarbonylsarcosine and N-benzyloxycarbonyl-beta-alanine, and they are reacted with 1,2'-N-benzyloxycarbonyl-6'-N-benzyl-6'-N-methylfortimicin B, tri-N-benzyloxycarbonyl-4-N-sarcosyl-6'-N-benzyl-6'-N-methylfortimicin B and tri-N-benzyloxycarbonyl-4-N-beta-alanyl-6'N-benzyl-6'-N-methylfortimicin B are respectively obtained.

Alternately, 1,2'-di-N-benzyloxycarbonylfortimicin B can be subjected to reductive alkylation in the presence of a lower aliphatic aldehyde such as formaldehyde, and the resulting product subjected to hydrolysis in the presence of an aldehyde scavenger such as hydroxylamine hydrochloride or methoxylamine hydrochloride, to obtain a 1,2'-di-N-benzyl- oxycarbonyl-6', 6'-di-N-loweralkylfortimicin B in which the 6'-loweralkyl groups are derived from the aldehyde chosen. For example, when the lower aliphatic aldehyde is formaldehyde, the product is 1,2'-di-N-benzyloxycarbonyl-6', 6'-di-N-methylfortimicin B. When the aliphatic aldehyde is acetaldehyde the product is 1,2'-di-N-benzyloxycarbonyl -6, 6-di-N-ethylfortimicin B. When the aliphatic aldehyde is propionaldehyde, the product is 1,2'-di-N-benzyloxycarbonyl -6',6'-di-N-propylfortimicin B, etc.

The 1,2'-di-N-benzyloxycarbonyl-6', 6'-di-N-alkyl-fortimicins B intermediate can be condensed with suitable acylating agents, as described above, to obtain the corresponding 4-N-acyl derivatives. For example, when the acylating agent is the N-hydroxysuccinimide ester of N-benzyloxycarbonylglycine, and is reacted with 1,2'-di-N-benzyloxycarbonyl -6',6'-di-N-methylfortimicin B, the resulting product is tri-N-benzyloxycarbonyl-6', 6'-di-N-dimethylfortimicin A. If the acylating agents are the N-hydroxysuccinimide esters of N-benzyloxycarbonylsarcosine and N-benzyloxycarbonyl -beta-alanine, and are, for example, reacted with 1,2'-di-N-benzyloxycarbonyl-6', 6'-di-N-methylfortimicin B, the products are tri-N-benzyloxycarbonyl-6', 6'-di-N-methyl-4-N-sarcosylfortimicin B and tri-N-benzyloxycarbonyl-6', 6'-di-N-dimethyl-4-N-beta-alanyl-fortimicin B, respectively.

Removal of the benzyloxycarbonyl or other aryloxycarbonyl protecting groups, as well as the benzyl or other aryl protecting groups is accomplished by hydrogenolysis, using a suitable catalyst, such as palladium or carbon. For example, when the 1,2'-di-N-benzyloxycarbonyl-6'-N-alkyl- 6'-N-benzylfortimicins of this invention are subjected to catalytic hydrogenolysis, in the presence of, for example, 5% palladium on carbon, the desired compound of Formula I are formed by replacement of the 6'-N-benzyl group and the benzyloxycarbonyl groups by hydrogen atoms to give 6'-N-alkylfortimicins which can be conveniently isolated as their acid chloride salts. For example, hydrogenolysis of 1,2'-di-N-benzyloxycarbonyl-6'-N-benzyl-6'-N-methylfortimicin B gives 6'-N-methylfortimicin B which can conveniently be isolated as the perhydrochloride salt. Similar hydrogenolysis of, for example, tri-N-benzyloxycarbonyl-6'-N-benzyl-6'-methylfortimicin A, tri-N-benzyloxycarbonyl-4-N-sarcosyl-6'-N-benzyl-6'-N-methylfortimicin B and tri-N-benzyloxycarbonyl-4-N-beta-alanyl 6'-N-benzyl-6'-N-methylfortimicin B yields 6'-N-methylfortimicin A, 4-N-sarcosyl-6'-N-methylfortimicin B, and 4-N-beta-alanyl-6'-N-methylfortimicin B, respectively.

Similarly, when the 1,2'-di-N-benzyloxycarbonyl-6',6'-di-N-loweralkylfortimicins are subjected to catalytic hydrogenolysis in the presence of a suitable catalyst, the benzyloxycarbonyl groups are replaced by hydrogen to give the desired 6',6'-di-N-loweralkylfortimicin. For example, catalytic hydrogenolysis of tri-N-benzyloxycarbonyl-6',6'-di-N-methylfortimicin B in the presence of 5% palladium on carbon in 0.2 N hydrochloric acid in methanol gives 6',6'-di-N-methylfortimicin B as the perhydrochloride salt. Similar hydrogenolysis of tri-N-benzyloxycarbonyl-6',6'-di-N-methylfortimicin A, tri-N-benzyloxycarbonyl-4-N-sarcosyl-6',6'-di-N-methylfortimicin B and tri-N-benzyloxycarbonyl-4-N-beta-alanyl-6',6'-di-N-methylfortimicin B results in the compounds 6',6'-di-N- dimethylfortimicin A, 4-N-sarcosyl-6',6'-di-N-methylfortimicin B, and 4-N-beta-alanyl-6',6'-di-N-methylfortimicin B, respectively, which can be isolated as, for example, their tetrahydrochloride salts.

The following examples further illustrate the present invention.

EXAMPLE 1

1,2'-Di-N-benzyloxycarbonylfortimicin B

To a magnetically stirred solution of 10 g. of fortimicin B, 150 ml. of water, 300 ml. of methanol, and 4.95 ml. of glacial acetic acid (solution pH 6), cooled to 0° in an ice bath, is added 15.7 g. of N-(benzyloxycarbonyloxy)succinimide. Stirring is then continued at 0° for 1.5 hours, and the solution is then allowed to stand at ambient temperature for 25 hours. The resulting solution is concentrated to one-third volume under vacuum and then extracted with chloroform. The chloroform solution is washed with 1% aqueous sodium bicarbonate and dried over anhydrous magnesium sulfate. The chloroform is evaporated under reduced pressure and residual solvent is removed by co-distillation with benzene under reduced pressure to give 19 g. of product. A sample of 96 g. of product prepared as above is chromatographed on a 7.0 cm O.D. (outside diameter) column packed to a height of 80 cm with a slurry of silica gel and a solvent system composed of chloroform: methanol: concentrated ammonium hydroxide (750:150:7). Elution is carried out with the solvent system yielding 36 g. of pure 1,2'-di-N-benzyloxycarbonylfortimicin B as a white powder: $[\alpha]_D^{22}+43°$ (c 1%, CH$_3$OH); NMR (CDCl$_3$)$\delta$0.81 d (C$_6$,—CH$_3$, J$_{6'7'}$=Hz), 2.32 (N—CH$_3$), 3.41; IR (CDCl$_3$) 3562, 3432, 1712 cm$^{-1}$.

Elemental analysis is in agreement with the empirical formula C$_{31}$H$_{44}$N$_4$O$_9$.

An additional 8.9 g. of 1,2'-di-N-benzyloxycarbonylfortimicin B of slightly lower purity is obtained from earlier chromatography fractions.

EXAMPLE 2

1,2'-Di-N-benzyloxycarbonyl-6'-N-benzylfortimicin B

A solution prepared from 0.617 g. of 1,2'-di-N-benzyloxycarbonylfortimicin B, 0.25 ml. of benzaldehyde, and 6.0 ml. of methanol is heated under reflux for 0.5 hours. To the resulting magnetically stirred solution, cooled to room temperature is added a freshly prepared solution of 0.1041 g. of sodium borohydride in 0.6 ml. of water. Stirring is continued at room temperature for 4 hours. The resulting solution is shaken with a mixture of 100 ml. of chloroform and 200 ml. of water. The chloroform solution is separated and washed with 200 ml. of water. The aqueous solutions are washed in series with three 100 ml. portions of chloroform. The chloroform solutions are combined and dried over anhydrous magnesium sulfate. Evaporation of the chloroform under reduced pressure leaves 0.816 g. of a sticky white glass. The product is chromatographed on 80 g. of silica gel packed to a height of 47 cm in a 2.4 cm O.D. column in a slurry with 160 ml. of a solvent system prepared from chloroform:methanol:concentrated ammonium hydroxide (19:1:0.2). Elution is carried out with the solvent system to yield 0.414 g. of 1,2'-di-N-benzyloxycarbonyl-6'-N-benzylfortimicin B: $[\alpha]_D^{23}+43°$ (c 1%, CH$_3$OH); NMR: (CDCl$_3$)$\delta$0.90 d (C$_6$', —CH$_3$, J$_{6',7'}$ 7 Hz); 2.37 (N—CH$_3$); 3.39 (OCH$_3$); IR: (CDCl$_3$) 3552, 3434, 3420, 1698 cm$^{-1}$ Elemental analysis is in agreement with the empirical formula C$_{38}$H$_{50}$N$_4$O$_9$.

EXAMPLE 3

1,2'-Di-N-benzyloxycarbonyl-6'-N-benzyl-6'-N-methylfortimicin B

A solution of 3 g. of 1,2'-di-N-benzyloxycarbonyl-6'-N-benzylfortimicin B in 220 ml. of methanol, in the presence of 10 ml. of 37% formalin and 3 g. of 5% platinum on carbon, is catalytically hydrogenated under three atmospheres of hydrogen for 6.5 hours. The catalyst is removed by filtration, and the solvent is removed under high vacuum leaving 2.71 g. of sticky, white glass. A sample of 2.4 g. of the product is chromatographed on 160 g. of silica gel packed to a height of 50 cm in a 3.4 cm O.D. column in a slurry with 320 ml. of a solvent system of methylene chloride:methanol:37% formalin. Elution is carried out with the solvent system to give 1.79 g. of the methylene, 4,5-oxazolidine derivative of 1,2'-di-N-benzyloxycarbonyl-6'-N-benzyl-6'-N-methylfortimicin B:

NMR (CDCl$_3$)$\delta$0.86 d (C$_6$'—CH$_3$, J$_{6',7'}$—6.8 Hz); 2.18, 2.30 (N—CH$_3$); 3.47 (OCH$_3$); 3.83d, 4.63d (—OCH$_2$NCH$_3$,J$_{AB}$=2.5 Hz).

A solution of 1.74 g. of the above prepared 4,5-oxazolidine derivative, 0.57 g. of hydroxylamine hydrochloride, 1.5 ml. of glacial acetic acid, and 100 ml. of methanol is heated under reflux for 0.5 hours. The major portion of the methanol is removed under reduced pressure and the residue is shaken with a mixture of dilute ammonium hydroxide and chloroform. The chloroform solution is separated and washed with saturated aqueous sodium chloride. The aqueous solutions are washed in series with three portions of chloroform.

The chloroform solutions are combined and dried over anhydrous magnesium sulfate. Evaporation of the chloroform under vacuum yields 1.69 g. of 1,2'-di-N-benzyloxycarbonyl-6'-N-benzyl-6'-N-methyl-fortimicin B.

$[\alpha]_D^{24}+39°$ (c 1%, CH$_3$OH); NMR: (CDCl$_3$)δ0.93 d (C$_{6'}$,—CH$_3$, J$_{6',7'}$=7 Hz); 2.15, 2.31 (N—CH$_3$), 3.42 (OCH$_3$); IR (CDCl$_3$) 3550, 3420, 1700 cm$^{-1}$.

Elemental analysis is in agreement with the empirical formula C$_{39}$H$_{52}$N$_4$O$_9$.

EXAMPLE 4

Tri-N-benzyloxycarbonyl-6'-N-benzyl-6'-N-methylfortimicin A

To a magnetically stirred solution of 0.706 g. of 1,2'-di-N-benzyloxycarbonyl-6'-N-benzyl-6'-N-methylfortimicin B in 9 ml. of tetrahydrofuran, cooled to 0° in an ice bath, is added 0.416 g. of the N-hydroxysuccinimide ester of N-benzyloxycarbonylglycine. Stirring is continued at 0° for 3 hours and then at ambient temperature for 20 hours. The resulting solution is shaken with a mixture of 200 ml. of 5% aqueous sodium bicarbonate and 200 ml. of chloroform. The chloroform solution is separated and washed with 200 ml. of water. The aqueous solutions are washed in series with three 100-ml. portions of chloroform. The chloroform solutions are combined and the chloroform is evaporated under reduced pressure leaving 1.00 g. of white glass. A sample of 0.97 g. of the product is chromatographed on 80 g. of silica gel packed to a height of 49 cm in a 2.4 cm O.D. column in a slurry with 160 ml of a solvent system of ethyl acetate:triethylamine (19.8:0.2). Elution was carried out with the solvent system to yield 0.768 g. of tri-N-benzyloxycarbonyl-6'-N-benzyl-6'-N-methyl-fortimicin A:

$[\alpha]_D^{22}+53°$ (c 1%, CH$_3$OH); NMR: (CDCl$_3$)δ1.01 d (C$_{6'}$,—CH$_3$, J$_{6',7}$=6.5 Hz); 2.17 (NCH$_3$CH$_2$Ph), 2.78 (NCH$_3$COCH$_2$NHZ), 3.28 (OCH$_3$); IR (CDCl$_3$) 3550, 3410, 1702, 1627 cm$^{-1}$.

Elemental analysis is in agreement with the empirical formula C$_{49}$H$_{61}$N$_5$O$_{12}$.

EXAMPLE 5

1,2'-Di-N-benzyloxycarbonyl-6',6'-di-N-dimethyl-fortimicin B

A solution prepared from 3.02 g. of 1,2-di-N-benzyloxycarbonylfortimicin B, 5 ml of 37% formalin, and 195 ml. of methanol is hydrogenated under 3 atmospheres of hydrogen for 4.5 hours in the presence of 1.5 g. of 5% platinum on carbon. The catalyst is removed by filtration and the solvent is evaporated under reduced pressure leaving 3.04 g. of product. The latter, in a solution with 5 ml. of formalin and 195 ml. of methanol, is hydrogenated under 3 atmospheres of 5% platinum or carbon. The catalyst is removed by filtration and the solvent is evaporated under reduced pressure, leaving 2.43 g. of the 4,5-methylene oxazolidine derivative of 1,2'-di-N-benzyloxycarbonyl-6',6'-di-N-methyl-fortimicin B:

NMR (CDCl$_3$)δ0.83d (C$_{6'}$, —CH$_3$, J$_{6',7'}$=8 Hz); 2.21, 3.32 N—CH$_3$) 3.48 (OCH$_3$); Doublet between 3.79–3.86, 4.50d (OCH$_2$NCH$_3$, J$_{AB}$=3 Hz)

A solution prepared from 2.37 g. of the above 4,5-methylene oxazolidine intermediate, 0.840 g. of hydroxylamine hydrochloride, 2.3 ml. of acetic acid and 150 ml. of methanol is heated under reflux for 0.5 hours. The major portion of the methanol is evaporated under reduced pressure and the residue is shaken with a mixture of 300 ml. of dilute ammonium hydroxide solution saturated with sodium chloride, and 200 ml. of chloroform. The chloroform solution is separated and washed with 300 ml. of saturated aqueous sodium chloride solution. The aqueous solutions are washed in series with three 100-ml. portions of chloroform. The chloroform solutions are combined and dried over anhydrous magnesium sulfate. Evaporation of the chloroform leaves 2.30 g. of white glass. The product is chromatographed on 200 g. of silica gel using a solvent system composed of methylene chloride:methanol:concentrated ammonium hydroxide (14:6:0.2) to yield 1.90 g. of 1,2'-di-N-benzyloxycarbonyl-6',6'-di-N-dimethylfortimicin B:

$[\alpha]_D^{22}+44°$ (c 1%, CH$_3$OH); NMR: (CDCl$_3$)δ0.84d (C$_{6'}$,—CH$_3$, J$_{6',7'}$=7 Hz) 2.18 [N(CH$_3$)$_2$], 2.37 (N—CH$_3$), 3.43 (OCH$_3$); IR (CDCl$_3$) 3557, 3423, 3348, 1695.

Elemental analysis is in agreement with the empirical formula C$_{33}$H$_{48}$N$_4$O$_9$.

EXAMPLE 6

Tri-N-benzyloxycarbonyl-6',6'-di-N-methylfortimicin A

To a magnetically stirred solution of 0.626 g. of 1,2'-di-N-benzyloxycarbonyl-6',6'-di-N-methylfortimicin B in 9 ml. of tetrahydrofuran, cooled in an ice bath, is added 0.4016 g. of the N-hydroxysuccinimide ester of N-benzyloxycarbonylglycine. Stirring is continued at 0° for 3 hours and then at ambient temperature for 22 hours. The resulting solution is shaken with a mixture of 200 ml. of chloroform and 200 ml. of 5% aqueous sodium bicarbonate. The chloroform solution is separated and washed in series with 200 ml. of water. The aqueous solutions are washed in series with three 100-ml. portions of chloroform. The chloroform solutions are combined and the chloroform is evaporated under reduced pressure leaving 0.8619 g. of white glass. The product is chromatographed on 75 g. of silica gel packed to a height of 46 cm in a 2.4 cm O.D. column in a slurry with 150 ml. of a solvent system of ethyl acetate:methanol:triethylamine (22:2:0.3). Elution is carried out with the solvent system to yield 0.7356 g. of tri-N-benzyloxycarbonyl-6',6'-di-N-methylfortimicin A as a white glass:

$[\alpha]_D^{22}+67°$ (c 1%), CH$_3$OH); NMR (CDCl$_3$)δ0.9d (C$_6$—CH$_3$, J$_{6',7'}$=6.7 Hz), 2.22 [N(CH$_3$)$_2$], 3.35 (N-CH$_3$-COCH$_2$NHZ), 3.31 (OCH$_3$); IR (CDCl$_3$) 3552, 3412, 1700, 1628 cm$^{-1}$.

Elemental analysis is in agreement with the empirical formula C$_{43}$H$_{57}$N$_5$O$_{12}$.

EXAMPLE 7

Tri-N-benzyloxycarbonyl-4-N-sarcosyl-6'-N-benzyl-6'-N-methylfortimicin B

To a magnetically stirred solution of 0.820 g. of 1,2'-di-N-benzyloxycarbonyl-6'-N-benzyl-6'-N-methylfortimicin B in 10 ml. of tetrahydrofuran, cooled in an ice bath, is added 0.480 g. of the N-hydroxysuccinimide ester of N-benzyloxycarbonylsarcosine. Stirring is continued at 0° for 3 hours and then at ambient temperature for 24 hours. The product is isolated by chloroform extraction and purified by chromatography on silica gel using an ethyl acetate:triethylamine system to give tri-N-benzyloxycarbonyl-4-N-sarcosyl-6'-N-benzyl-6'-N-methylfortimicin B. IR, NMR and elemental analysis are compatible with the structure.

EXAMPLE 8

Tri-N-benzyloxycarbonyl-4-N-beta-alanyl-6'-N-benzyl-6'-N-methylfortimicin B

To a magnetically stirred solution of 0.960 g. of 1,2'-di-N-benzyloxycarbonyl-6'-N-benzyl-6'-N-methylfortimicin B in 12 ml. of tetrahydrofuran, cooled in an ice bath, is added 0.594 g. of the N-hydroxysuccinimide ester of N-benzyloxycarbonyl-beta-alanine. Stirring is continued at 0° for 3 hours and then at ambient temperature for 27 hours. The product is isolated by chloroform extraction and purified by chromatography on silica gel using an ethyl acetate:triethylamine system to give tri-N-benzyloxycarbonyl-4-N-beta-alanyl-6'-N-benzyl-6'-N-methylfortimicin B. IR, NMR and elemental analysis are compatible with the structure.

EXAMPLE 9

Tri-N-benzyloxycarbonyl-4-N-sarcosyl-6,6'-di-N-methylfortimicin B

To a magnetically stirred solution of 0.920 g. of 1,2'-di-N-benzyloxycarbonyl-6',6'-di-N-methylfortimicin B in 12 ml. of tetrahydrofuran, cooled in an ice bath, is added 0.640 g. of the N-hydroxysuccinimide ester of N-benzyloxycarbonylsarcosine. Stirring is continued at 0° for 3 hours and then at ambient temperature for 22 hours. The product is isolated by chloroform extraction and purified by chromatography on silica gel using an ethyl acetate:methanol:triethylamine system to give tri-N-benzyloxycarbonyl-4-N-sarcosyl-6',6'-di-N-methylfortimicin B. IR, NMR and elemental analysis are compatible with the structure.

EXAMPLE 10

Tri-N-benzyloxycarbonyl-4-N-beta-alanyl-6',6'-di-N-methylfortimicin B

To a magnetically stirred solution of 0.885 g. of 1,2'-di-N-benzyloxycarbonyl-6',6'-di-N-methylfortimicin B in 12 ml. of tetrahydrofuran, cooled in an ice bath, is added 0.609 g. of the N-hydroxysuccinimide ester of N-benzyloxycarbonyl-beta-alanine. Stirring is continued at 0° for 3 hours and then at ambient temperature for 25 hours. The product is isolated by chloroform extraction and purified by chromatography on silica gel using a chloroform:methanol:triethylamine system to give tri-N-benzyloxycarbonyl-4-N-beta-alanyl-6',6'-di-N-methylfortimicin B. IR, NMR, and elemental analysis are compatible with the structure.

EXAMPLE 11

6'-N-Methylfortimicin A Tetrahydrochloride

A sample of 0.432 g. of tri-N-benzyloxycarbonyl-6'-N-benzyl-6'-N-methylfortimicin A in the presence of 28.4 ml. of 0.2 N hydrochloric acid in methanol, 6.6 ml. of methanol, 0.430 g. of 5% palladium on carbon is hydrogenated for 4 hours under 3 atmospheres of hydrogen. The catalyst is removed by filtration and the solvent is evaporated under reduced pressure leaving 0.259 g. of 6'-N-methylfortimicin A as the tetrahydrochloride salt in the form of a powder:

$[\alpha]_D^{23}+81°$ (c 1%, CH$_3$OH); NMR: (D$_2$O)$\delta$1.81d (C$_{6'}$—CH$_3$, J$_{6',7'}$=7 Hz); 3.20 (N$^+$H$_2$CH$_3$), 3.58 (NCH$_3$COCH$_2$N$^+$H$_3$), 3.95 (OCH$_3$) IR(KBr) 1630 cm$^{-1}$.

EXAMPLE 12

6'-N-Methylfortimicin B Tetrahydrochloride

A sample of 0.260 g. of 1,2'-di-N-benzyloxycarbonyl-6'-N-benzyl-6'-N-methylfortimicin B in the presence of 36 ml. of 0.2 N hydrochloric acid in methanol, 14 ml. of methanol and 0.260 g. of 5% palladium on carbon is hydrogenated for 4 hours under 3 atmospheres of hydrogen. The catalyst is removed by filtration and the solvent is evaporated under reduced pressure leaving 0.172 g. of 6'-N-methylfortimicin B as the tetrahydrochloride salt in the form of a powder:

$[\alpha]_D^{23}+81°$ (c 1%, CH$_3$OH); NMR (D$_2$O)$\delta$1.80 (C$_{6'}$—CH$_3$, J$_{6',7'}$=6.8 Hz), 3.21, 3.28 (N$^+$H$_2$CH$_3$), 3.95 (OCH$_3$)

The mass spectrum is compatible with the empirical formula C$_{16}$H$_{34}$N$_4$O$_5$.

EXAMPLE 13

6',6'-Di-N-methylfortimicin B tetrahydrochloride

A sample of 0.407 g. of 1,2'-di-N-benzyloxycarbonyl-6',6'-di-N-methylfortimicin B in the presence of 50 ml. of 0.2 N hydrochloric acid in methanol and 0.4 g. of 5% palladium on carbon is hydrogenated for 4 hours under 3 atmospheres of hydrogen. The catalyst is removed by filtration and the solvent is evaporated under reduced pressure leaving 0.304 g. of 6',6'-di-N-methylfortimicin B as the tetrahydrochloride salt in the form of a powder:

$[\alpha]_D^{24}+84°$ (c 1%, CH$_3$OH); NMR: (D$_2$O)$\delta$1.76 (C$_{6'}$—CH$_3$, J$_{6',7'}$=6.6 Hz), 3.29, 3.38 [N$^+$H(CH$_3$)$_2$], 3.38 (N$^+$H$_2$CH$_3$), 3.95 (OCH$_3$).

The mass spectrum is compatible with the empirical formula C$_{17}$H$_{36}$N$_4$O$_5$.

EXAMPLE 14

6',6'-Di-N-methylfortimicin A tetrahydrochloride

A sample of 0.350 g. of tri-N-benzyloxycarbonyl-6',6'-di-N-methylfortimicin A in the presence of 33.5 ml. of 0.2 N-hydrochloric acid in methanol, 1.5 ml. of methanol, 0.350 g. of 5% palladium on carbon is hydrogenated for 4 hours under 3 atmospheres of hydrogen. The catalyst is removed by filtration and the solvent is evaporated under reduced pressure leaving 0.2445 g. of 6',6'-di-N-methylfortimicin A as the tetrahydrochloride salt in the form of a white powder:

$[\alpha]_D^{23}+77°$, (c 1%, CH$_3$OH); NMR: (D$_2$O)$\delta$1.76 (C$_{6'}$—CH$_3$, J$_{6',7'}$=6.4 Hz); 3.36, 3.37 [N$^+$H(CH$_3$)$_2$]; 3.58 (NCH$_3$COCH$_2$N$^+$H$_3$), 3.94 (OCH$_3$); IR (KBr) 1634.

The mass spectrum is in agreement with the empirical formula C$_{19}$H$_{39}$N$_5$O$_6$.

EXAMPLE 15

4-N-beta-Alanyl-6'-N-methylfortimicin B Tetrahydrochloride

Tri-N-benzyloxycarbonyl-4-N-beta-alanyl-6'-N-methylfortimicin B is converted to 4-N-beta-alanyl-6'-N-methylfortimicin B and isolated as the hydrochloride salt according to the process of Example 11.

NMR, IR and the Mass Spectrum are compatible with the spectrum.

EXAMPLE 16

4-N-Sarcosyl-6'-N-methylfortimicin B Tetrahydrochloride

Tri-N-benzyloxycarbonyl-4-N-sarcosyl-6'-N-benzyl-6'-N-methylfortimicin B is converted to 4-N-sarcosyl-6'-N-methylfortimicin B and isolated as the tetrahydrochloride salt according to the procedure of Example 11.

NMR, IR, and the mass spectrum are compatible with the structure.

EXAMPLE 17

4-N-beta-Alanyl-6',6'-di-N-methylfortimicin B Tetrahydrochloride

Tri-N-benzyloxycarbonyl-4-N-beta-alanyl-6',6'-N-methylfortimicin B is converted to 4-N-beta-alanyl-6',6'-di-N-methylfortimicin B and isolated as the tetrahydrochloride salt according to the process of Example 11.

NMR, IR, and the mass spectrum are compatible with the structure.

EXAMPLE 18

4-N-Sarcosyl-6',6'-di-N-methylfortimicin B Tetrahydrochloride

Tri-N-benzyloxycarbonyl-4-N-sarcosyl-6',6'-di-N-methylfortimicin B is converted to 4-N-sarcosyl-6',6'-di-N-methylfortimicin B, isolated as the tetrahydrochloride salt according to the process of Example 11.

NMR, IR, and the mass spectrum are compatible with the structure.

EXAMPLE 19

In vitro Antibiotic Activities of Representative Representative 6'-N-alkyl substituted fortimicins The in vitro antibiotic activities of the tetrahydrochloride salts of fortimicin B, 6'-6'-di-N-methyl-fortimicin B, 6'-N-methylfortimicin A and 6',6'-di-N-methylfortimicin A were determined by a two-fold agar dilution method using Mueller-Hinton agar, 10 ml. per Petri plate. The agar was inoculated with one loopful (0.001 ml. loop) of a 1:10 dilution of a 24 hour broth culture of the indicated test organism and incubated at 37° C. for 24 hours. The activities are listed in Table 1. Minimum inhibitory concentrations (MIC) are expressed as mcg/ml.

tion. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredients in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 1 to 100 mg/kg of body weight daily are administered to a mammalian patient suffering from an infection caused by susceptible organisms.

TABLE I

| ORGANISM | MINIMUM INHIBITORY CONCENTRATION (mcg/ml) | | | |
| --- | --- | --- | --- | --- |
| | 6'-N-Methyl-Fortimicin A .4HCl | 6'6'-di-N-Methyl-Fortimicin .4HCl | 6'-N-Methyl Fortimicin B .4HCl | 6',6'-di-N-Methyl Fortimicin B .4HCl |
| *Escherichia coli* R$_3$ | 3.1 | >500 | >890 | >760 |
| *Streptococcus faecalis* ATCC10541 | 25 | >500 | >890 | >760 |
| *Pseudomouas aerugiuosa* BMH #1 | 12.5 | >500 | >890 | >760 |
| *Staphlococcus aureus* ATCC6538P | 0.1 | 7.8 | 27.8 | 95 |
| *Escherichia coli* ATCC26 | 0.78 | 500 | 111.3 | >760 |
| *Bacillus subtilis* U of I11 10707 | 0.2 | 31.3 | 27.8 | 47.5 |
| *Proteus vulgaris* ATCC6897 | 1.6 | >500 | 890 | >760 |
| *Shigella sonnei* ATCC9290 | 0.78 | >500 | 222.5 | >760 |
| *Salmonella typhi* ATCC9992 | 0.39 | 125 | 55.6 | 380 |
| *Klebsiella pneumoniae* ATCC10031 | 0.1 | 31.3 | 55.6 | 190 |

The compounds of this invention are active as systemic antibiotics when injected by parenteral routes of administration, i.e., by the intramuscular, intravenous, intraperitoneal or subcutaneous routes of administra-

We claim:
1. A compound of the formula

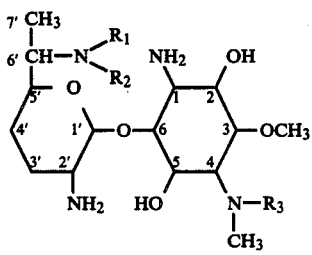

wherein $R_1$ is loweralkyl, $R_2$ is hydrogen or loweralkyl and $R_3$ is selected from the group consisting of hydrogen acyl of the formula

wherein R is loweralkyl, hydroxyacyl, aminoacyl, N-monoloweralkyl-aminoacyl, N,N-diloweralkylaminoacyl, hydroxy-substituted aminoacyl, aminoacyl, an aminoacid residue, loweralkyl, hydroxyloweralkyl, aminoloweralkyl, N-monoloweralkylaminoloweralkyl, N,N-diloweralkylaminoloweralkyl, or hydroxy-substituted aminoloweralkyl, and the pharmaceutically acceptable salts thereof.

2. A compound of claim 1 wherein $R_3$ is hydrogen.
3. A compound of claim 1 wherein $R_3$ is glycyl.
4. A compound of claim 1 wherein $R_3$ is loweralkyl.
5. A compound of claim 1 wherein $R_3$ *is acyl.*
6. A compound of claim 1 wherein $R_3$ is selected from the group consisting of aminoacyl, N-monoloweralkylaminoacyl-N,N-diloweralkylaminoacyl, or hydroxy-substituted aminoacyl.
7. A compound of claim 1 wherein $R_3$ is an amino acid residue.
8. A compound of claim 2: 6'-N-methylfortimicin B or a pharmaceutically acceptable salt thereof.
9. A compound of claim 2: 6'-N-ethylfortimicin B or a pharmaceutically acceptable salt thereof.
10. A compound of claim 2: 6',6'-N,N-dimethylfortimicin B or a pharmaceutically acceptable salt thereof.
11. A compound of claim 3: 6'-N-methylfortimicin A or a pharmaceutically acceptable salt thereof.
12. A compound of claim 3: 6',6'-N,N-dimethylfortimicin A or a pharmaceutically acceptable salt thereof.
13. A compound of claim 7: 4-N-beta-alanyl-6'-N-methylfortimicin B or a pharmaceutically acceptable salt thereof.
14. A compound of claim 7: 4-N-sarcosyl-6'-N-methylfortimicin B or a pharmaceutically acceptable salt thereof.
15. A compound of claim 7: 4-N-beta-alanyl-6',6'-N,N-dimethylfortimicin B or a pharmaceutically acceptable salt thereof.
16. A compound of claim 7: 4-N-sarcosyl-6',6'-N,N-dimethylfortimicin B or a pharmaceutically acceptable salt thereof.
17. A compound of the formula

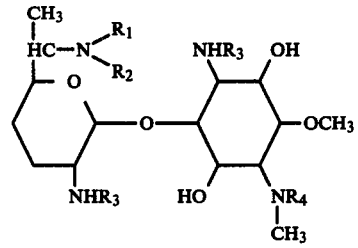

wherein $R_1$ is monocyclicaryl or loweralkyl, $R_2$ is hydrogen or lower alkyl, each $R_3$ is monocyclic aryloxycarbonyl and $R_4$ is hydrogen, monocyclic aryloxyacyl or

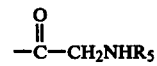

wherein $R_5$ is hydrogen or monocyclic aryloxycarbonyl.
18. A compound of claim 17, wherein $R_1$ is monocyclicaryl.
19. A compound of claim 17, wherein $R_1$ is benzyl.
20. A compound of claim 17, wherein each $R_3$ is benzyloxycarbonyl.
21. A compound of claim 17, wherein $R_1$ is monocyclicaryl and each $R_3$ is monocyclicaryl.
22. A compound of claim 21, wherein $R_1$ is benzyl and each $R_3$ is benzyloxycarbonyl.
23. A compound of claim 22, wherein $R_1$ is benzyl, each $R_3$ is benzyloxycarbonyl and $R_5$ is benzyloxycarbonyl.
24. A compound of claim 17, wherein $R_1$ is benzyl, $R_2$ is hydrogen and each $R_3$ is benzyloxycarbonyl.
25. A compound of claim 17, wherein $R_1$ is benzyl, $R_2$ is loweralkyl and each $R_3$ is benzyloxycarbonyl.
26. A compound of claim 17, wherein $R_1$ is loweralkyl and $R_2$ is hydrogen.
27. A compound of claim 17, wherein $R_1$ is loweralkyl, $R_2$ is loweralkyl and each $R_3$ is benzyloxycarbonyl.
28. A compound of claim 17: 1,2'-di-N-benzyloxycarbonyl-6'-N-benzyl-6'-N-methylfortimicin B.
29. A pharmaceutical composition comprising a therapeutically effective amount of a compound of claim 1 and a pharmaceutically acceptable carrier or diluent.

* * * * *

UNITED STATES PATENT AND TRADEMARK OFFICE
CERTIFICATE OF CORRECTION

PATENT NO. : 4,205,070
DATED : May 27, 1980
INVENTOR(S) : John S. Tadanier, et. al.

It is certified that error appears in the above—identified patent and that said Letters Patent is hereby corrected as shown below:

In claim 6, lines 2 and 3, "N-mono-loweralkylaminoacyl-N,N-diloweralkylaminoacyl" should read - - N-monoloweralkylaminoacyl, N,N-diloweralkylaminoacyl - - .

At column 3, line 23, "$R_4$" should read - - $R_3$ - - .

Signed and Sealed this

Second Day of March 1982

[SEAL]

Attest:

GERALD J. MOSSINGHOFF

Attesting Officer    Commissioner of Patents and Trademarks